(12) United States Patent
Kim et al.

(10) Patent No.: US 11,426,211 B2
(45) Date of Patent: Aug. 30, 2022

(54) ARTICULATING CONNECTORS, SYSTEMS, AND METHODS THEREOF

(71) Applicant: GLOBUS MEDICAL, INC., Audubon, PA (US)

(72) Inventors: Allen Kim, Philadelphia, PA (US); Ross Morris, Norristown, PA (US); Daniel Spangler, Green Lane, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 17/082,779

(22) Filed: Oct. 28, 2020

(65) Prior Publication Data
US 2022/0125486 A1 Apr. 28, 2022

(51) Int. Cl.
*A61B 17/70* (2006.01)

(52) U.S. Cl.
CPC ...... *A61B 17/7043* (2013.01); *A61B 17/7032* (2013.01); *A61B 17/7034* (2013.01); *A61B 17/7037* (2013.01)

(58) Field of Classification Search
CPC ............ A61B 17/7041; A61B 17/7043; A61B 17/7049; A61B 17/705; A61B 17/7052
See application file for complete search history.

(56) References Cited

U.S. PATENT DOCUMENTS

| 5,474,551 | A * | 12/1995 | Finn ................... A61B 17/7035 606/264 |
| 6,234,705 | B1 * | 5/2001 | Troxell ............. A61B 17/7052 403/237 |
| 6,283,967 | B1 | 9/2001 | Troxell et al. |
| 6,306,137 | B2 | 10/2001 | Troxell |
| 6,554,832 | B2 | 4/2003 | Shluzas |
| 7,717,940 | B2 | 5/2010 | Woods et al. |
| 7,744,633 | B2 | 6/2010 | Berrevoets et al. |
| 7,862,587 | B2 * | 1/2011 | Jackson ............. A61B 17/7028 606/246 |
| 7,927,355 | B2 | 4/2011 | Berrevoets et al. |
| 8,361,117 | B2 | 1/2013 | Michielli et al. |
| 8,758,411 | B1 | 6/2014 | Rayon et al. |
| 8,828,055 | B2 | 9/2014 | Blain et al. |
| 8,870,921 | B2 | 10/2014 | Michielli et al. |
| 9,107,703 | B2 | 8/2015 | Torres |
| 9,131,964 | B2 | 9/2015 | Blain et al. |
| 9,381,044 | B2 | 7/2016 | Robinson et al. |
| 9,468,469 | B2 | 10/2016 | Otte et al. |
| 9,468,471 | B2 | 10/2016 | Otte et al. |
| 9,572,601 | B2 | 2/2017 | Stenulson et al. |
| 9,668,779 | B2 | 6/2017 | Okamoto |
| 9,949,768 | B2 | 4/2018 | Rathbun et al. |

(Continued)

*Primary Examiner* — Lynnsy M Summit

(57) ABSTRACT

Connector assemblies, systems, and methods thereof. An articulating connector has a first end that clamps to a first rod in an existing construct and a second end having a second end that clamps to a second rod in a new construct or such that the new construct can be extended from the existing construct. In the case of different sized constructs used in different areas of the spine, an articulating connector has a first end that clamps to a first rod in a new construct having rods of a first size and a second end having a second end that clamps to a second rod in a new construct having rods of a second size. The clamping portions are capable of translating and rotating with respect to each other.

14 Claims, 9 Drawing Sheets

(56) References Cited

U.S. PATENT DOCUMENTS

| | | |
|---|---|---|
| 10,251,678 B2 | 4/2019 | Alsup et al. |
| 10,271,878 B2 | 4/2019 | Courtney et al. |
| 10,357,290 B2 | 4/2019 | Torres |
| 2007/0156142 A1* | 7/2007 | Rezach .............. A61B 17/7038 606/252 |
| 2018/0280062 A1* | 10/2018 | Lee ..................... A61B 17/705 |
| 2018/0280063 A1 | 10/2018 | Lee et al. |
| 2021/0177468 A1* | 6/2021 | Murray .............. A61B 17/7002 |

* cited by examiner

ARTICULATING CONNECTORS, SYSTEMS, AND METHODS THEREOF

BACKGROUND

Field of the Invention

The present invention relates to rod connectors, such as spinal hardware connectors.

Description of the Related Art

At times, spinal surgeons may be required to add additional fixation to spinal segments adjacent to previously instrumented spinal segments or levels. In these cases, the hardware from the initial surgery may interfere with placement of new fixation for the adjacent level. Therefore, there is a need for connector implants that attach to the existing spinal fusion construct on one end and extend fixation to adjacent levels in need of fusion.

In other situations, spinal surgeons may be required to cross the cervical-thoracic junction when instrumenting spinal segments or levels in a primary surgery or a revision surgery. In these cases hardware in the thoracic region of the spine is larger than the hardware in the cervical region of the spine. Therefore, there is a need for connector implants that attach to both smaller, cervical hardware and larger, thoracic hardware.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The present disclosure relates to components, systems, and methods for connecting one device to another device. For example, one elongate implant, such as a first rod, may be coupled to another elongate implant, such as a second rod. The elongate implants, such as rods, are well known to connect adjacent vertebrae in a spinal fusion procedure. Depending on the configuration of rods or implants, it may be desirable to have one rod connected to another rod or additional implant. In the case of two or more rods, these rods may be interconnected with one or more connectors, for example, in a single primary surgery, such as a multi-level spinal operation, or at a later surgery, for example, in a revision surgery. In a multi-level spinal operation, such as a cervical-thoracic surgery, spinal surgeons may be required to cross the cervical-thoracic junction when instrumenting spinal segments or levels in a primary surgery or a revision surgery. In these cases hardware in the thoracic region of the spine is larger than the hardware in the cervical region of the spine and the connectors can accommodate for the changes in instrumentation sizes. In a revision surgery, connectors can be used to connect new fixation constructs to existing fixation constructs without the need to remove the original hardware. The different connection modes provided in the following exemplary embodiments offer a range of options to be chosen based on a specific clinical scenario and/or surgeon preference. Although certain configurations are shown herein, it is envisioned that any suitable number, type, and selection of connectors and implants may be chosen and configured by the skilled surgeon.

According to one embodiment, a modular connector system includes a connector having a body having a first clamping portion and a second clamping portion. The first clamping portion has a passage defined by two legs having a longitudinal axis extending therethrough and being sized to allow a first rod to be inserted therein, a bottom portion having an opening, and a securing mechanism comprising a set screw capable of engaging the two legs. The second clamping portion has a passage defined by two legs having a longitudinal axis extending therethrough and being sized to allow a second rod to be inserted therein, a bottom portion having a projection capable of being received in the opening of the first clamping portion, and a securing mechanism comprising a set screw capable of engaging the two legs. The securing mechanism of the first clamping portion having an unlocked position configured to receive the first rod and a locked position configured to releasably secure the first rod in the opening between the two opposing legs of the clamp and in the passage. The securing mechanism of the second clamping portion functions identically to the securing mechanism of the first clamping portion.

In another embodiment, a modular connector system includes a connector having a body having a first clamping portion and a second clamping portion. The first clamping portion has a passage defined by two legs having a longitudinal axis extending therethrough and being sized to allow a first rod to be inserted therein, a bottom portion having an opening, and a securing mechanism comprising a set screw capable of engaging the two legs. The second clamping portion has an open headed connector defining a passage having a longitudinal axis extending therethrough and being sized to allow a second rod to be inserted therein. The open headed connector includes a second passage for receiving a securing mechanism, such as a set screw, to clamp the second rod in the passage of the open headed connector.

In yet another embodiment, a modular connector system includes a connector having a body having a first clamping portion and a second clamping portion. The first clamping portion has a passage defined by two legs having a longitudinal axis extending therethrough and being sized to allow a first rod to be inserted therein, a bottom portion having an opening, and a securing mechanism comprising a set screw capable of engaging the two legs. The second clamping portion has a closed headed connector defining an enclosed passage having a longitudinal axis extending therethrough and being sized to allow a second rod to be inserted therein. The open headed connector may include a second passage for receiving a securing mechanism, such as a set screw, to clamp the second rod in the passage of the closed headed connector.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

DETAILED DESCRIPTION

Figure 1:
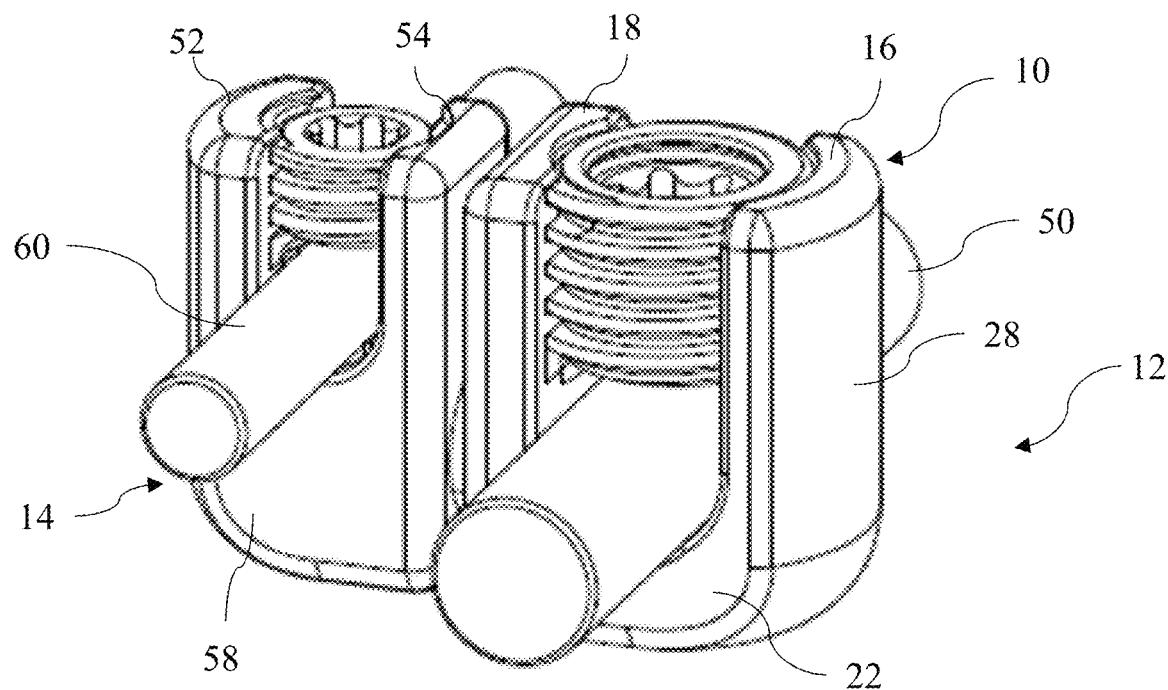
FIG. 1 is a perspective view of an articulating connector according to a first exemplary embodiment.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

The present disclosure relates to components, systems, and methods for connecting one elongate implant, such as a first rod, to another elongate implant, such as a second rod. The elongate implants, such as rods, are well known to connect adjacent vertebrae in a spinal fusion procedure. Depending on the configuration of rods or implants, it may be desirable to have one rod connected to another rod or additional implant. In the case of two or more rods, these rods may be interconnected with one or more connectors, for example, in a single given surgery, such as a multi-level spinal operation, or at a later surgery, for example, in a revision surgery.

For example, connectors can be used to connect instrumentation of different sizes used in different areas of the spine or connectors can be used to connect new fixation constructs to existing fixation constructs without the need to remove index surgery hardware. A benefit to such direct attachment to existing constructs saves operating time, causes less disruption to the patient, and minimizes patient healing time. The ability of the inventive connectors to maintain connection with existing constructs can maximize utility in cases of varying patient anatomy and existing spinal constructs. The different connection modes provided in the following exemplary embodiments offer a range of options to be chosen based on a specific clinical scenario and/or surgeon preference. Thus, although certain configurations are shown herein, it is envisioned that any suitable number, type, and selection of connectors and implants, such as rods, may be chosen and configured by the skilled surgeon.

While the different connection modes disclosed herein can be used independently, those skilled in the art will recognize that the connection modes can be combined "à la carte" according to patient needs. Further, while the connection modes disclosed herein can be provided separately, kits that include various and multiple combinations of different connection modes can also be provided.

Figure 2:
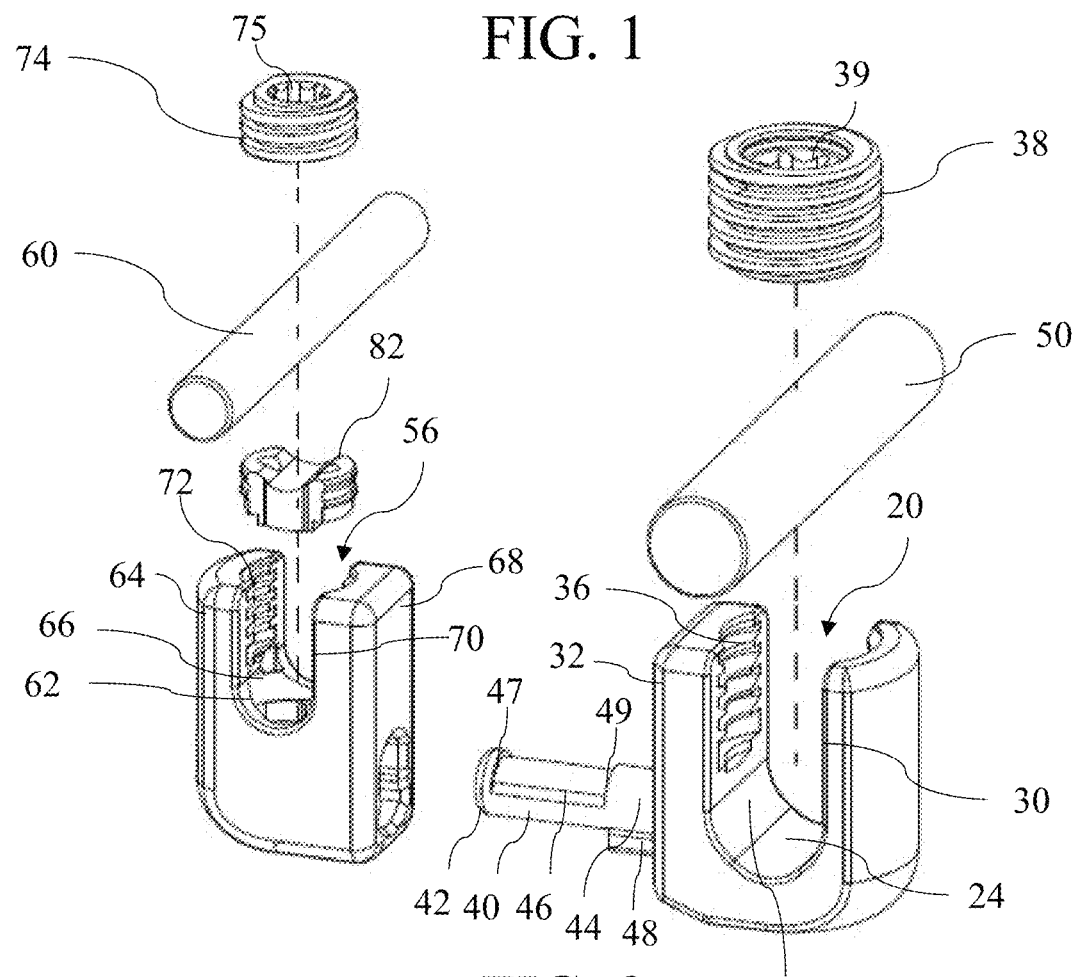
FIG. 2 is an exploded view of the articulating connector shown in FIG. 1.

Referring to FIGS. 1-2, an articulating connector assembly 10 ("connector assembly 10") according to a first exemplary embodiment is shown. Connector assembly 10 is used to attach to a first rod 50 that, for example, is already present in an existing construct or part of a larger instrumented set, to a second rod 60. Although not shown, it should be understood that first rod 50 and/or second rod 60 can be supported by and secured to one or more other implants such as hooks or pedicle screws. U.S. patent application Ser. No. 16/392,947, the entire disclosure of which is incorporated by reference herein, discloses exemplary embodiments of connectors connecting to rods and other implants.

In an exemplary embodiment, connector assembly 10 includes a first clamping portion or rod acceptor 12 that is coupled to a second clamping portion or tulip 14. In a preferred embodiment, the rod acceptor and tulip 12, 14 are rotatably coupled to each other such that the rod acceptor and tulip 12, 14 can rotate or articulate with respect to each other, but remain coupled or otherwise connected. It is further contemplated that in an exemplary embodiment, the rod acceptor and tulip 12, 14 can also translate with respect to each other while remaining coupled or otherwise connected. Once the desired rotational and/or translational position is achieved, the rod acceptor 12 can be secured to tulip 14, locking the articulation, i.e., locking the rotation and/or translation.

Turning to rod acceptor 12, in an exemplary embodiment, rod acceptor 12 includes two upstanding legs 16, 18 that define there between an open passageway 20 for receiving a rod, such as rod 50. The legs 16, 18 are connected at a lower end by a base 22. An upper surface 24 of the base may be configured and dimensioned to approximate the shape of the rod to be received in the passageway 20. For example, upper surface 24 of base 22 may include a curved surface to approximate the curvature of the outer surface of a cylindrical rod or may be planar to approximate the planar surface of a rectangular rod. It is contemplated that the upper surface 24 may also include other shapes that do not approximate the outer surface of the rod received in the passageway 20.

In an exemplary embodiment, leg 16 includes an outer surface 28 and an inner surface 30 and leg 18 includes an outer surface 32 and an inner surface 34. In an exemplary embodiment, outer surface 28 and inner surface 30 may be curved such that outer surface 28 is convexly curved and inner surface 30 is concavely curved. Inner surface 34 may also be concavely curved while outer surface 32 is preferably planar. The inner surfaces 30, 32 proximate the upper end of the legs 16, 18 may include engagement structures 36 such as threads or ratchet teeth. The engagement structures 36 are designed to engage with a securing mechanism 38, such as a locking screw or locking cap, which has corresponding engagement features. In an exemplary embodiment, securing mechanism 38 also includes an opening 39 that includes a female interface that is capable of being engaged by a male interface of an insertion or installation instrument (not shown). In practice, once the rod 50 is received within passageway 20 between legs 16, 18, the securing mechanism 38 is engaged with the engagement structures 36. This provisionally couples the rod 50 to the rod acceptor 12. Once the rod acceptor 12 is positioned at the desired location on rod 50, the securing mechanism 38 is then further tightened locking the rod acceptor 12 onto the rod 50.

Focusing on FIG. 2, extending from the base 22 of rod acceptor 12 is a projection 40. In an exemplary embodiment, projection 40 has a first end 42, a second end 44 and is generally cylindrical. Although projection 40 is generally cylindrical, other shapes are contemplated. Positioned near the first end 42 of the projection 40 and extending towards the second end 44 is a cutout 46. Adjacent to projection 40 is an extension 48, which also extends away from base 22. In an exemplary embodiment, extension 48 is connected to and extends downwardly from projection 40 and is shorter in length than projection 40. It is contemplated that projection 40 and extension 48 are formed as a monolith.

Turning to the tulip 14, in an exemplary embodiment, tulip includes two upstanding legs 52, 54 that define there between an open passageway 56 for receiving a rod, such as rod 60. In an exemplary embodiment, rods 50 and 60 may be sized differently according to their usage, but it is contemplated that they can be the same size. For example, rod 60 may be used in a cervical construct while rod 50 may be used in a thoracic construct, thus, rod 60 will be smaller than rod 50. It should be noted that when discussing the relative size of the rods, it is the not the length, rather it is the other dimensions, such as circumference or width and height, that are being compared. The legs 52, 54 are connected at a lower end by a base 58. At least a portion of an upper portion 62 of the base may be configured and dimensioned to approximate the shape of the rod to be received in the passageway 56. For example, a portion of an upper portion 62 of base 58 may include a curved surface to approximate the curvature of the outer surface of a cylindrical rod or may be planar to approximate the planar surface of a rectangular rod. It is contemplated that the upper portion 62 may also include other shapes that do not approximate the outer surface of the rod received in the passageway 56.

In an exemplary embodiment, leg 52 includes an outer surface 64 and an inner surface 66 and leg 54 includes an outer surface 68 and an inner surface 70. In an exemplary embodiment, outer surface 64 and inner surface 66 may be curved such that outer surface 64 is convexly curved and inner surface 66 is concavely curved. Inner surface 70 may also be concavely curved while outer surface 68 is preferably planar. The inner surfaces 66, 70 proximate the upper end of the legs 52, 54 may include engagement structures 72 such as threads or ratchet teeth. The engagement structures 72 are designed to engage with a securing mechanism 74, such as a locking screw or locking cap, which has corresponding engagement features. In an exemplary embodiment, securing mechanism 74 also includes an opening 75 that includes a female interface that is capable of being engaged by a male interface of an insertion or installation instrument (not shown). In practice, once the rod 60 is received within passageway 56 between legs 52, 54, the securing mechanism 74 is engaged with the engagement structures 72. This provisionally couples the rod 60 to the tulip 14. Once the tulip 14 is positioned at the desired location on rod 60, the securing mechanism 74 is then further tightened locking the tulip 14 onto the rod 60.

With reference to FIGS. 2-5, the base 58 of the tulip 14 includes a first opening 76 that extends from the outer surface 68 toward the outer surface 64. It is contemplated that the first opening 76 may extend all the way through the base 58 of the tulip 14 such that it extends into outer surface 64 forming a through opening or it may extend only partially through the base 58 of the tulip 14 forming a blind opening or blind hole. The first opening 76 is configured and dimensioned to receive at least a portion of the projection 40. In fluid communication with the first opening 76 and passageway 56 is a second opening 78. In an exemplary embodiment, the second opening 78 extends generally perpendicular to the first opening 76 from the first opening 76 to the passageway 56. A third opening 80 also extends from the outer surface 68 toward the outer surface 64. In an exemplary embodiment, the third opening 80 extends only partly through tulip 14. The third opening 80 is configured and dimensioned to receive at least a portion of the extension 48. The third opening 80 is in fluid communication with the first opening 76 and modifies the shape of the first opening 76 such that the first and third openings 76 and 80 form a generally "keyhole" shape. This "keyhole" shaped opening operatively engages the projection 40 and extension 48 as further explained below.

Figure 6:
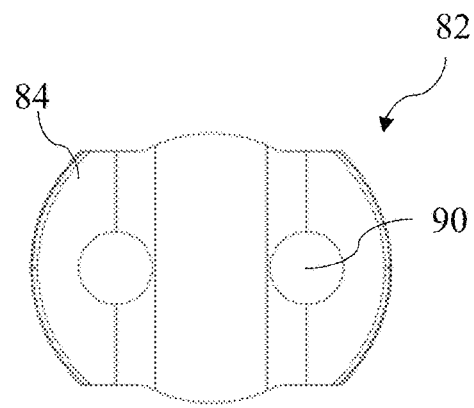
FIG. 6 is top view of a saddle of the tulip shown in FIG. 2.
Figure 7:
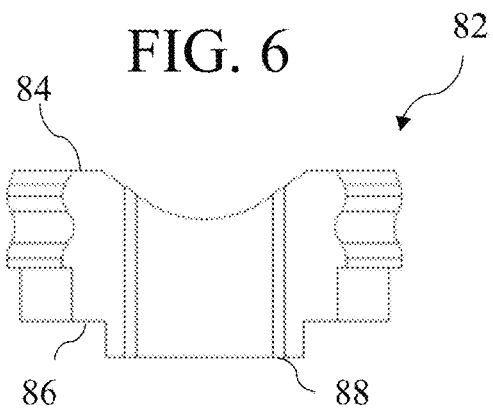
FIG. 7 is side view of the saddle of the tulip shown in FIG. 2.
Figure 8A:
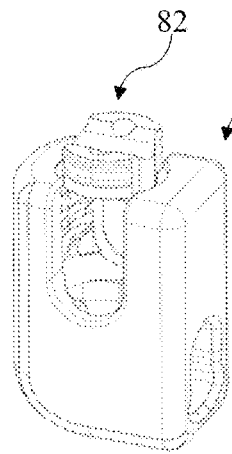
FIGS. 8A-8D are perspective views of the first and second clamping portions of the articulating connector shown in FIG. 1 during assembly.
Figure 8B:
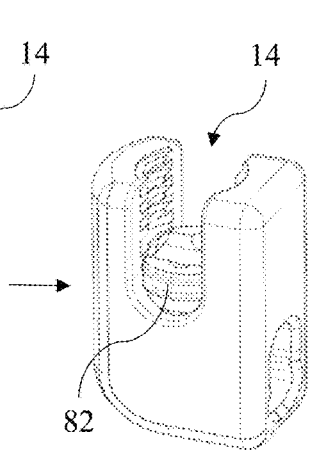
Figure 8C:
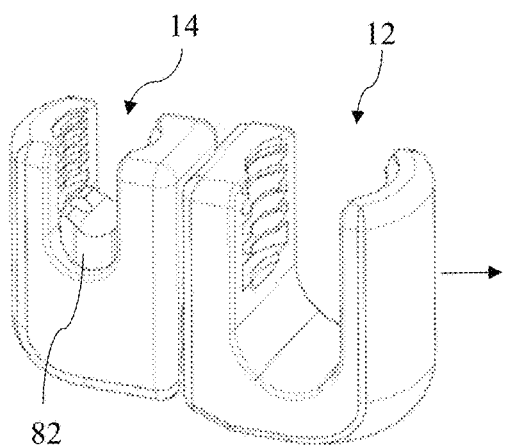
Figure 8D:
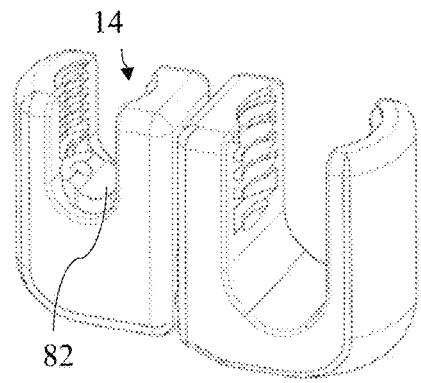
Figure 9A:
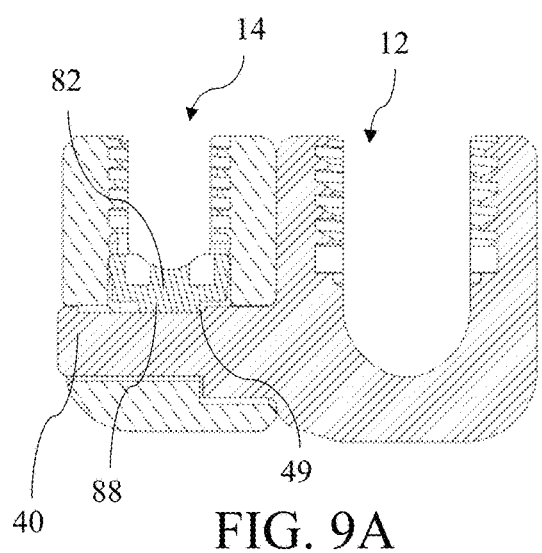
FIGS. 9A-9B are cross sectional side views of the articulating connector shown in FIG. 1 showing translation between the first and second clamping portions of the articulating connector.
Figure 9B:
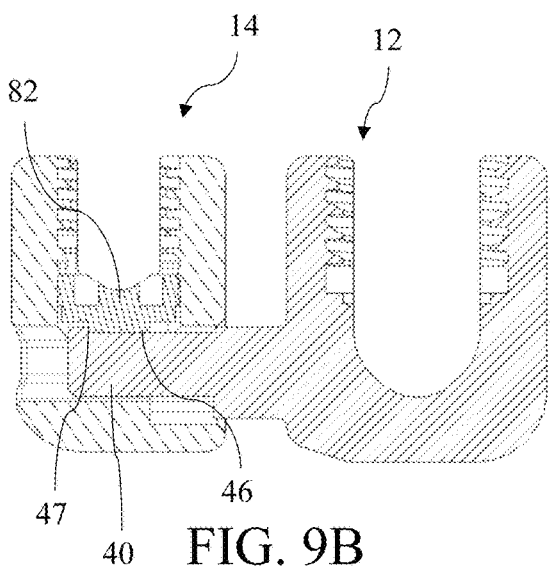
Figure 10A:
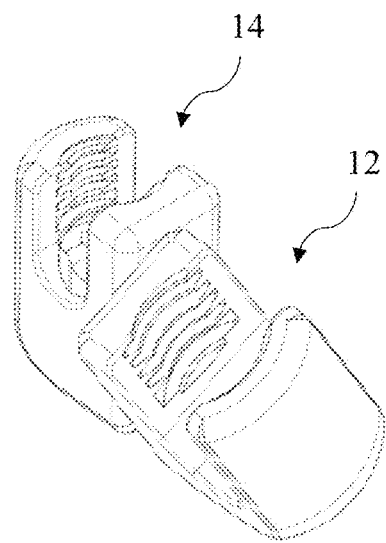
FIGS. 10A-10C are perspective views of the articulating connector shown in FIG. 1 showing rotation between the first and second clamping portions of the articulating connector.
Figure 10B:
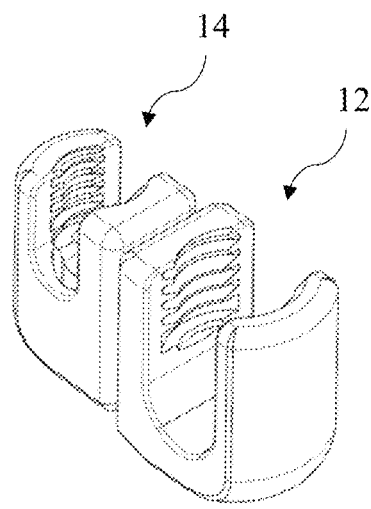
Figure 10C:
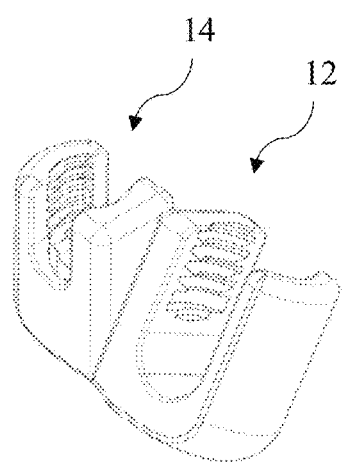
Figure 11A:
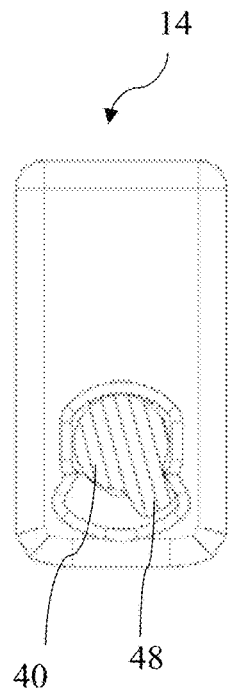
FIGS. 11A-11C are partial cross sectional side views of the articulating connector shown in FIGS. 10A-10C.
Figure 11B:
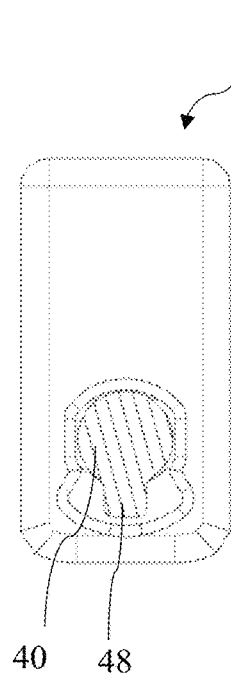
Figure 11C:
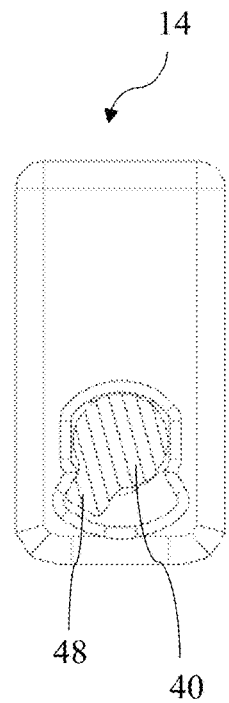

In an exemplary embodiment, a saddle 82 is received and positioned within the second opening 78. As best seen in FIGS. 6 and 7, the saddle 82 has an upper surface 84 that is at least in part shaped to approximate the outer shape of the rod 60. In an exemplary embodiment, rod 60 is cylindrical so the upper surface 84 of the saddle 82 includes a concavely curved portion that is sized to accommodate the rod 60. The saddle 82 also has a lower surface 86 that includes a step 88. The step 88 is designed to engage with the cutout 46 of the projection 40. The saddle 82 also may include at least one blind hole or opening 90. In an exemplary embodiment, when saddle 82 is installed in opening 78 in the tulip 14, the saddle 82 can still translate in opening 78.

Figure 3:
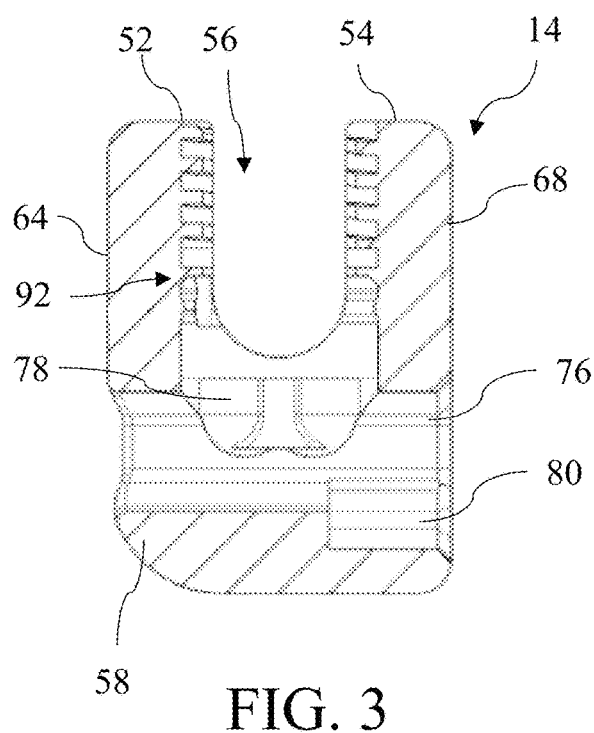
FIG. 3 is a side cross sectional view of a second clamping portion of the articulating connector shown in FIG. 2.
Figure 4:
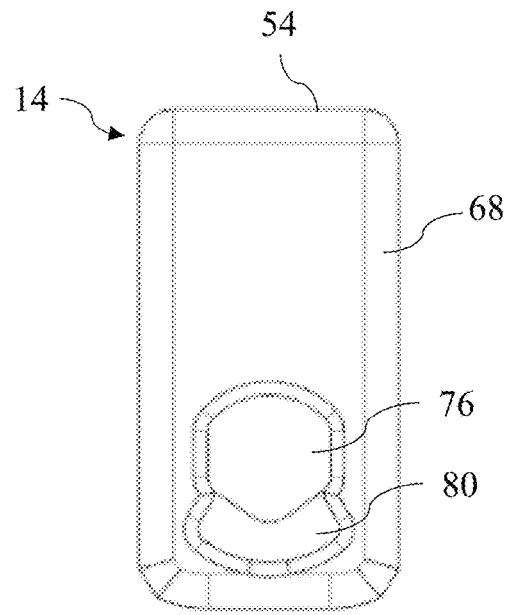
FIG. 4 is a side view of the second clamping portion of the articulating connector shown in FIG. 2.
Figure 5:
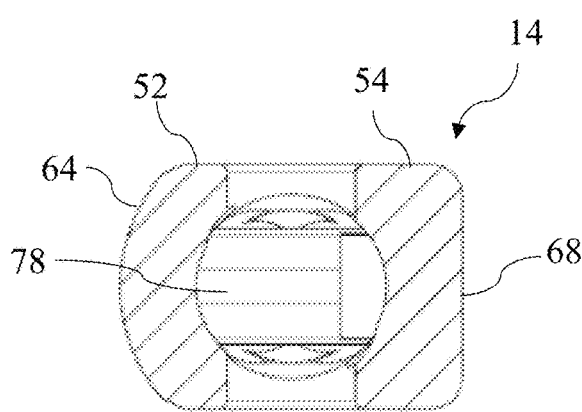
FIG. 5 is a top cross section view of the second clamping portion of the articulating connector shown in FIG. 2.

With reference to FIGS. 8A-8D, the at least one blind hole 90 is designed to engage an instrument that can rotate the saddle 82 when it is installed in the tulip 14 during manufacturing of the connector assembly 10. As best seen in FIG. 3, tulip 4 also includes at least on relief cut 92. The relief cuts 92 function to reduce the force needed to rotate the saddle 82 when it is installed in the tulip 14. FIG. 8 shows the assembly of the components of the connector assembly 10 in four sequential illustrations. During assembly, the saddle 82 is received in the opening 78 in tulip 14 in a first position. The rod acceptor 12 is then engaged to the tulip 14 by having the projection 40 and the extension 48 respectively received within the first and third openings 76, 80. Once the projection 40 and the extension 48 are received in the first and third openings 76, 80, the saddle 82 is rotated 90 degrees and pushed further into the tulip 14 to a second position. In this second position, the saddle 82 operatively couples the rod acceptor 12 to the tulip 14 such that the rod acceptor 12 and the tulip 14 can translate and rotate with respect to each other but cannot decouple from each other.

More specifically and with reference to FIGS. 8A-8D, 9A and 9B, as the saddle 82 is rotated and seated in the second opening 78 in the tulip 14, the step 88 engages with the cutout 46 of the projection 40. The step 88 will limit the amount of translation of the rod acceptor 12 with respect to the tulip 14 since the step 88 will either abut the proximal end or edge 47 or the medial end or edge 49 of the cutout 46 as the rod acceptor 12 translates toward or away from the tulip 14.

Regarding the limited rotation, with reference to FIGS. 10A-10C and 11A-11C, with the projection 40 and the extension 48 positioned inside the first opening 76 and the third opening 80, the rod acceptor 12 can rotate relative to the tulip 14. The rotation of the rod acceptor 12 relative to the tulip 14 is limited by the shape and dimension of the third opening 80. As the rod acceptor 12 is rotated, the extension 48 will abut the edges of the third opening 48 limiting the rotational travel of the rod acceptor 12 with respect to the tulip 14. In an exemplary embodiment, the rotational travel is limited to 30 degrees in each direction.

In an exemplary use, the tulip 14 and the rod acceptor 12 are adjusted, both translationally and rotationally, so that the rods 50 and 60 can be received within the passageways 20 and 56, respectively. Once the rod 60 is received within passageway 56 between legs 52, 54, the securing mechanism 74 is engaged with the engagement structures 72. This provisionally couples the rod 60 to the tulip 14. Similarly, once the rod 50 is received within passageway 20 between legs 16, 18, the securing mechanism 38 is engaged with the engagement structures 36. This provisionally couples the rod 50 to the rod acceptor 12. Once the tulip 14 is positioned at the desired location on rod 60, the securing mechanism 74 is then further tightened locking the tulip 14 onto the rod 60. As the securing mechanism 74 is further tightened, the securing mechanism 74 pushes on the rod 60, which, in turn, pushes on the saddle 82. Saddle 82 translates downwardly pushing against the projection 40 locking the rod acceptor 12 both translationally and rotationally with respect to the tulip 14. In an exemplary embodiment, a tightening instrument may be used to engage opening 75 to further tighten the securing mechanism 74. Similarly, once the rod acceptor 12 is positioned at the desired location on rod 50, the securing mechanism 38 is then further tightened locking the rod acceptor 12 onto the rod 50. In an exemplary embodiment, a tightening instrument may be used to engage opening 39 to further tighten the securing mechanism 38. It should be noted that there is no order in the process of locking the rods 50 and 60 to the rod acceptor 12 and the tulip 14 and locking the rod acceptor 12 to the tulip 14.

Figure 12:
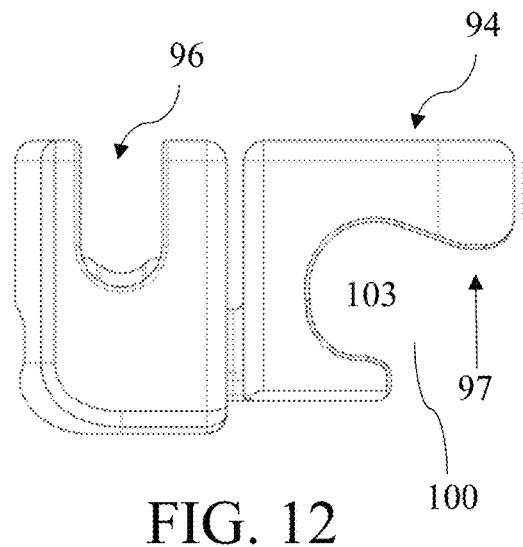
FIG. 12 is a side view of an articulating connector according to a second exemplary embodiment.
Figure 13:
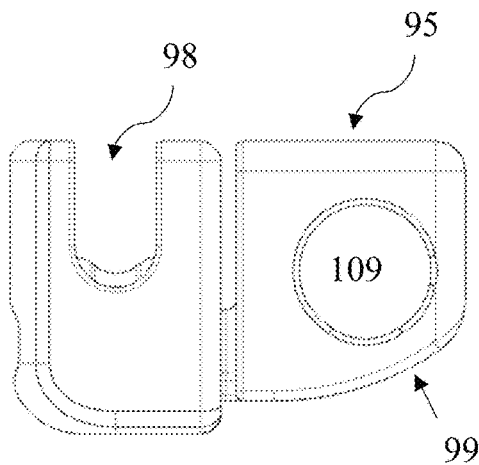
FIG. 13 is a side view of an articulating connector according to a third exemplary embodiment.
Figure 14A:
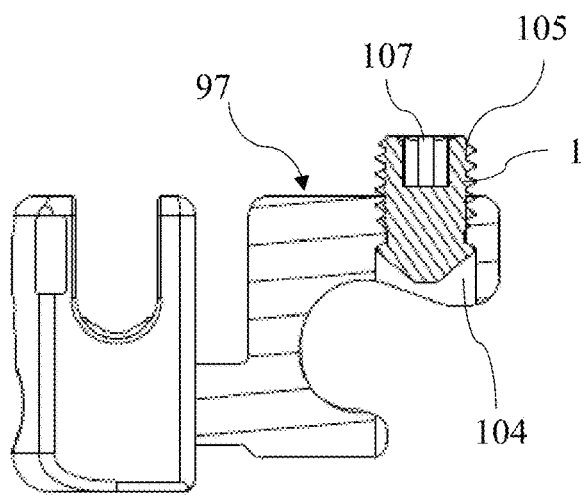
FIG. 14A is a partial cross sectional side view of the articulating connector shown in FIG. 12.

Turning to FIGS. 12 and 13, other exemplary embodiments of articulating connectors 94, 95 are contemplated. FIG. 12 shows an articulating connector 94 that includes a second clamping portion or tulip 96 and a first clamping portion or open rod acceptor 97 while FIG. 13 shows an articulating connector 95 that includes a second clamping portion or tulip 98 and a first clamping portion or closed rod acceptor 99. Since the articulating connectors 94, 95 are nearly identical to the articulating connector 10 both in terms of the constituent components and the functionality, only the differences will be highlighted herein. The open rod acceptor 97 includes an opening 100 that is in fluid communication with a passageway 103. The passageway 103 is configured and dimensioned to receive a rod, such as the rod 50. Since the opening 100 is positioned on a lateral side of the open rod acceptor 97, the open rod acceptor is able to engage a rod laterally providing an alternate option for rod engagement. With reference to FIGS. 12 and 14A, the open rod acceptor 97 also includes an opening 104 that, in an exemplary embodiment, is threaded to threadably receive a locking screw 105. The locking screw 105 includes threads 106 and an opening 107 to engage with an insertion instrument. In an exemplary embodiment, the locking screw 105 is threadably driven or advanced into opening 104 after a rod is received in passageway 103 to lock the rod with respect to open rod acceptor 97 and articulating connector 94.

Figure 14B:
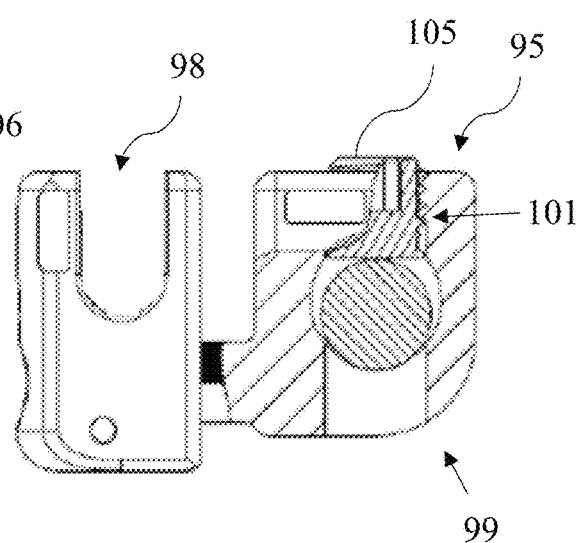
FIG. 14B is a partial cross sectional side view of the articulating connector shown in FIG. 13.

With reference to FIGS. 13 and 14B, the closed rod connector 99 includes a passageway 109 which is configured and dimensioned to receive a rod, such as the rod 50. Since the passageway 109 of the closed rod connector 99 does not include an access opening for the rod, the rod can only be received in the passageway 109 axially. Once the rod, such as rod 50, is received within the passageway, a locking screw, such as locking screw 105, which is threadably received in an opening 101 can be advanced in the opening to lock the rod to the closed rod connector 99.

Figure 15:
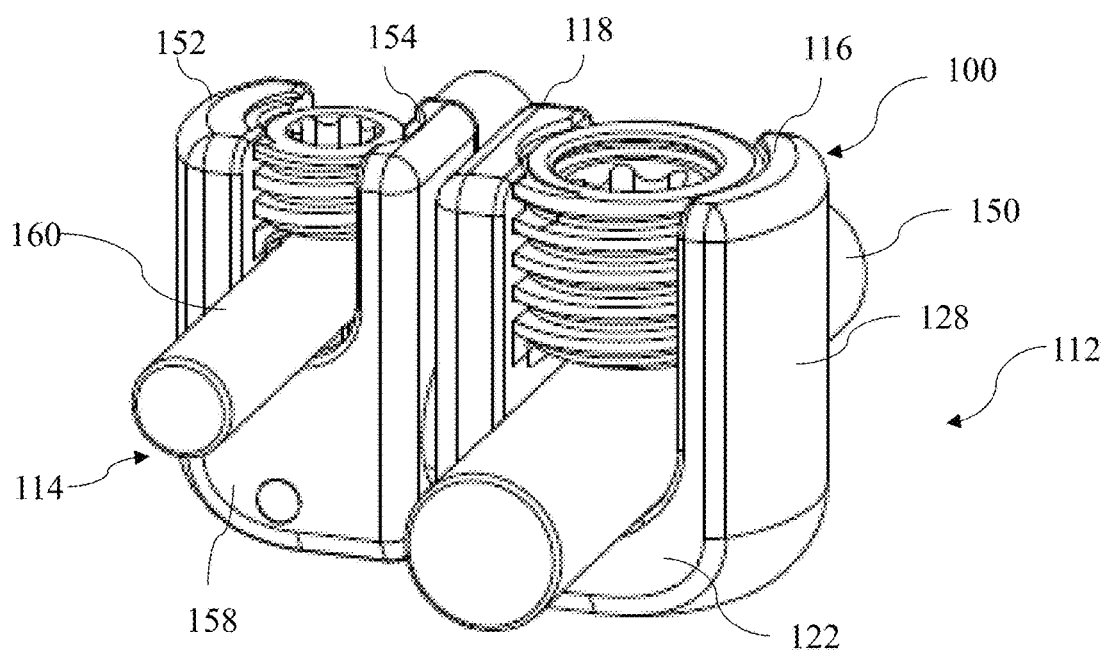
FIG. 15 is a perspective view of an articulating connector according to a fourth exemplary embodiment.
Figure 16:
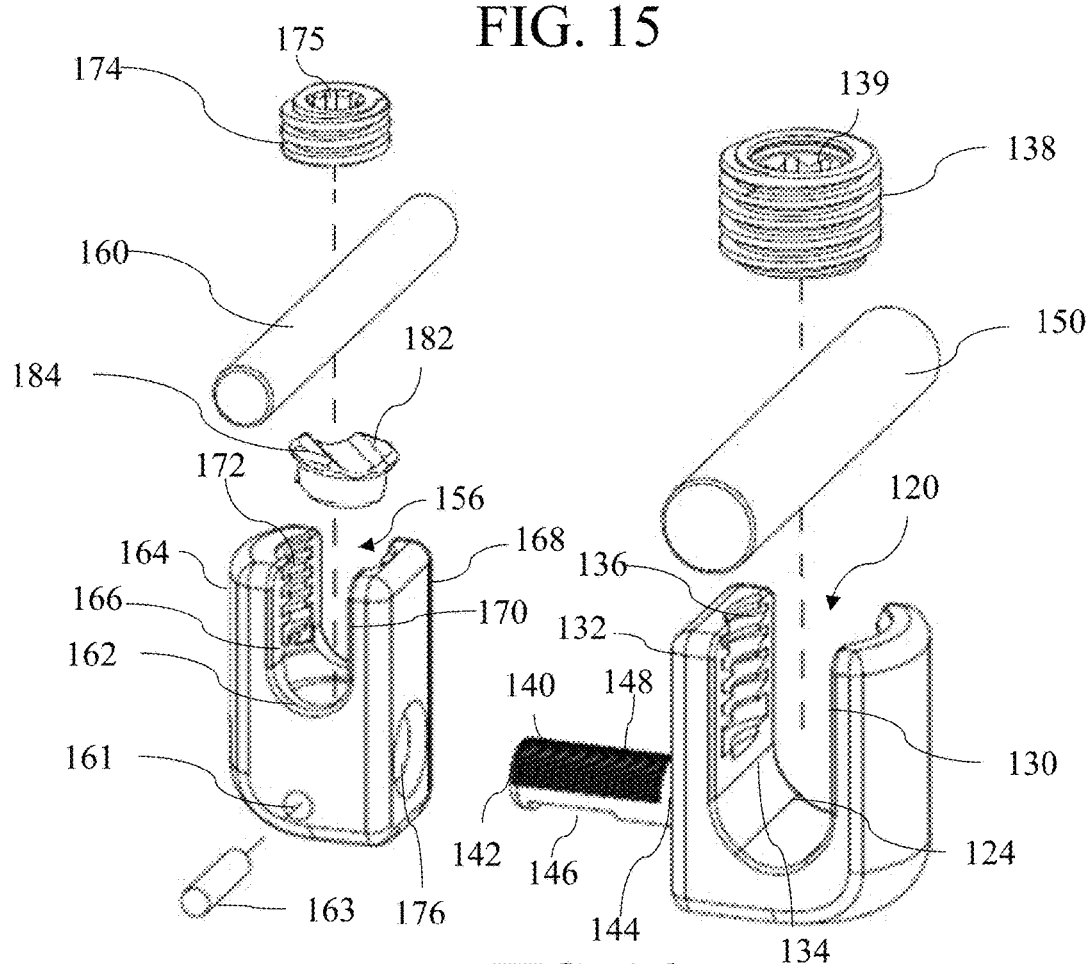
FIG. 16 is an exploded view of the articulating connector shown in FIG. 15.

Referring now to FIGS. 15-16, an articulating connector assembly 100 ("connector assembly 100") according to a second exemplary embodiment is shown. Connector assembly 100 is used to attach to a first rod 150 that, for example, is already present in an existing construct or part of a larger instrumented set, to a second rod 160. Although not shown, it should be understood that first rod 150 and/or second rod 160 can be supported by and secured to one or more other implants such as hooks or pedicle screws.

In an exemplary embodiment, connector assembly 100 includes a first clamping portion or rod acceptor 112 that is coupled to a second clamping portion or tulip 114. In a preferred embodiment, the rod acceptor and tulip 112, 114 are rotatably coupled to each other such that the rod acceptor and tulip 112, 114 can rotate or articulate with respect to each other, but remain coupled or otherwise connected. It is further contemplated that in an exemplary embodiment, the rod acceptor and tulip 112, 114 can also translate with respect to each other while remaining coupled or otherwise connected. Once the desired rotational and/or translational position is achieved, the rod acceptor 112 can be secured to tulip 114, locking the articulation, i.e., locking the rotation and/or translation.

Turning to the rod acceptor 112, in an exemplary embodiment, the rod acceptor 112 includes two upstanding legs 116, 118 that define there between an open passageway 120 for receiving a rod, such as rod 150. The legs 116, 118 are connected at a lower end by a base 122. An upper surface 124 of the base may be configured and dimensioned to approximate the shape of the rod to be received in the passageway 120. For example, upper surface 124 of base 122 may include a curved surface to approximate the curvature of the outer surface of a cylindrical rod or may be planar to approximate the planar surface of a rectangular rod. It is contemplated that the upper surface 124 may also include other shapes that do not approximate the outer surface of the rod received in the passageway 120.

In an exemplary embodiment, leg 116 includes an outer surface 128 and an inner surface 130 and leg 118 includes an outer surface 132 and an inner surface 134. In an exemplary embodiment, outer surface 128 and inner surface 130 may be curved such that outer surface 128 is convexly curved and inner surface 130 is concavely curved. Inner surface 134 may also be concavely curved while outer surface 132 is preferably planar. The inner surfaces 130, 134 proximate the upper end of the legs 116, 118 may include engagement structures 136 such as threads or ratchet teeth. The engagement structures 136 are designed to engage with a securing mechanism 138, such as a locking screw or locking cap, which has corresponding engagement features. In an exemplary embodiment, securing mechanism 138 also includes an opening 139 that includes a female interface that is capable of being engaged by a male interface of an insertion or installation instrument (not shown). In practice, once the rod 150 is received within passageway 120 between legs 116, 118, the securing mechanism 138 is engaged with the engagement structures 136. This provisionally couples the rod 150 to the rod acceptor 112. Once the rod acceptor 112 is positioned at the desired location on rod 150, the securing mechanism 138 is then further tightened locking the rod acceptor 112 onto the rod 150.

Focusing on FIG. 16, extending from the base 122 of rod acceptor 12 is a projection 140. In an exemplary embodiment, projection 140 has a first end 142, a second end 144 and is generally cylindrical. Although projection 140 is generally cylindrical, other shapes are contemplated. Positioned near the first end 142 of the projection 140 and extending towards the second end 144 is a cutout 146. In an exemplary embodiment, the side of the projection 140 that is opposite to the cutout 146 is textured. The texturing 148 may be teeth, knurling, indentations or other surface roughening/projections.

Turning to the tulip 114, in an exemplary embodiment, tulip includes two upstanding legs 152, 154 that define there between an open passageway 156 for receiving a rod, such as rod 160. In an exemplary embodiment, rods 150 and 160 may be sized differently according to their usage, but it is contemplated that they can be the same size. For example, rod 160 may be used in a cervical construct while rod 150 may be used in a thoracic construct, thus, rod 160 will be smaller than rod 150. It should be noted that when discussing the relative size of the rods, it is the not the length, rather it is the other dimensions, such as circumference or width and height, that are being compared. The legs 152, 154 are connected at a lower end by a base 158. At least a portion of an upper portion 162 of the base may be configured and dimensioned to approximate the shape of the rod to be received in the passageway 156. For example, a portion of an upper portion 162 of base 158 may include a curved surface to approximate the curvature of the outer surface of a cylindrical rod or may be planar to approximate the planar surface of a rectangular rod. It is contemplated that the upper portion 162 may also include other shapes that do not approximate the outer surface of the rod received in the passageway 156. A lower portion of the base 158 includes an opening 161 which may be a blind opening or a through opening. The opening 161 is sized and configured to receive a pin 163. The pin 163 may extend partly or all the way through the opening 161.

In an exemplary embodiment, leg 152 includes an outer surface 164 and an inner surface 166 and leg 154 includes an outer surface 168 and an inner surface 170. In an exemplary embodiment, outer surface 164 and inner surface 166 may be curved such that outer surface 164 is convexly curved and inner surface 166 is concavely curved. Inner surface 170 may also be concavely curved while outer surface 168 is preferably planar. The inner surfaces 166, 170 proximate the upper end of the legs 152, 154 may include engagement structures 172 such as threads or ratchet teeth. The engagement structures 172 are designed to engage with a securing mechanism 174, such as a locking screw or locking cap, which has corresponding engagement features. In an exemplary embodiment, securing mechanism 174 also includes an opening 175 that includes a female interface that is capable of being engaged by a male interface of an insertion or installation instrument (not shown). In practice, once the rod 160 is received within passageway 156 between legs 152, 154, the securing mechanism 174 is engaged with the engagement structures 172. This provisionally couples the rod 60 to the tulip 114. Once the tulip 114 is positioned at the desired location on rod 160, the securing mechanism 174 is then further tightened locking the tulip 114 onto the rod 160.

Figures 17A, 17B:
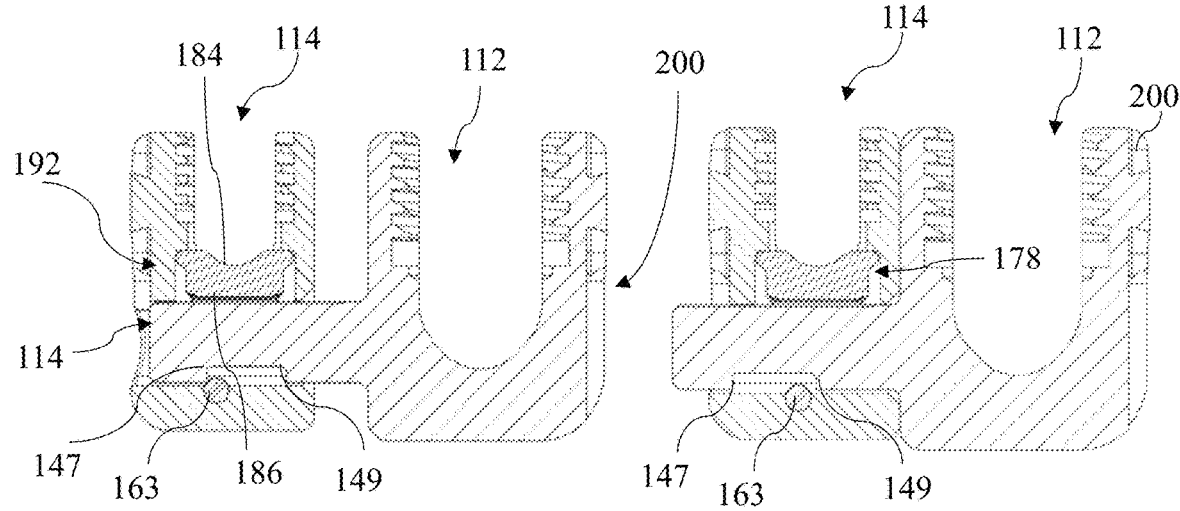
FIGS. 17A-B are cross sectional side views of the articulating connector shown in FIG. 15 showing translation between the first and second clamping portions of the articulating connector.

With reference to FIGS. 16-17B, the base 158 of the tulip 114 includes a first opening 176 that extends from the outer surface 168 toward the outer surface 164. It is contemplated that the first opening 176 may extend all the way through the base 158 of the tulip 114 such that it extends into outer surface 164 forming a through opening or it may extend only partially through the base 158 of the tulip 114 forming a blind opening or blind hole. The first opening 176 is configured and dimensioned to receive at least a portion of the projection 140. In fluid communication with the first opening 176 and passageway 156 is a second opening 178. In an exemplary embodiment, the second opening 178 extends generally perpendicular to the first opening 176 from the first opening 176 to the passageway 156.

Figure 20A:
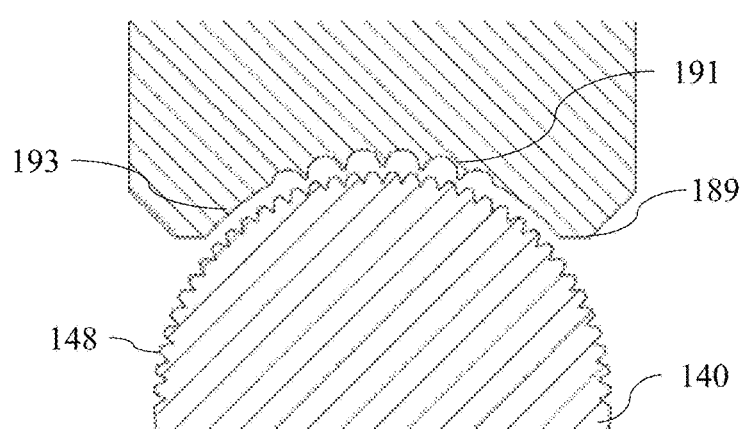
FIGS. 20A-B are focused cross sectional views of various components of the articulating connector shown in FIG. 15.
Figure 20B:
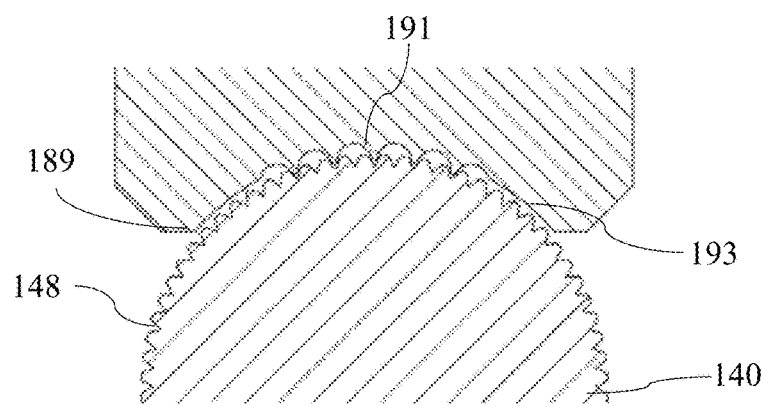

In an exemplary embodiment, a saddle 182 is received and positioned within the second opening 178. As best seen in FIGS. 16 and 17A-B, the saddle 182 has an upper surface 184 that is at least in part shaped to approximate the outer shape of the rod 160. In an exemplary embodiment, rod 160 is cylindrical so the upper surface 184 of the saddle 182 includes a concavely curved portion that is sized to accommodate the rod 160. The saddle 182 also has a lower surface 186 that may be flat or may include a step (similar to step 88 on saddle 82). In an exemplary embodiment, the lower surface 189 (and/or step) has is at least in part shaped to approximate the outer shape of the projection 140. The lower surface 189 (and/or step) is designed to engage with the texturing portion 148 of the projection 40. This is best seen in FIGS. 20A-B. In an exemplary embodiment, lower surface 189 (and/or step) can also include texturing 191 which can engage texturing 148 to provide additional gripping. In an exemplary embodiment, flats 193 may be included on one or both sides of the texturing 191. The flats 193 help prevent angulation binding of the projection 140 when received in the opening 176 prior to final tightening. In an exemplary embodiment, when saddle 182 is installed in opening 178 in the tulip 114, the saddle 182 can still translate in opening 178.

Although not shown here, but can be seen in the embodiment shown in FIG. 2, the saddle 182 also may include at least one blind hole or opening 190. In an embodiment that uses a saddle 182 with at least one blind hole 190, the at least one blind hole 190 is designed to engage an instrument that can rotate the saddle 182 when it is installed in the tulip 114 during manufacturing of the connector assembly 110. As best seen in FIG. 17A, tulip 114 includes at least one relief cut 192. The relief cuts 192 function to reduce the force needed to rotate the saddle 182 when it is installed in the tulip 114. FIG. 8 can be used as a reference for the assembly of the components of the connector assembly when used with a saddle 182 having at least one blind hole 190.

Figure 19:
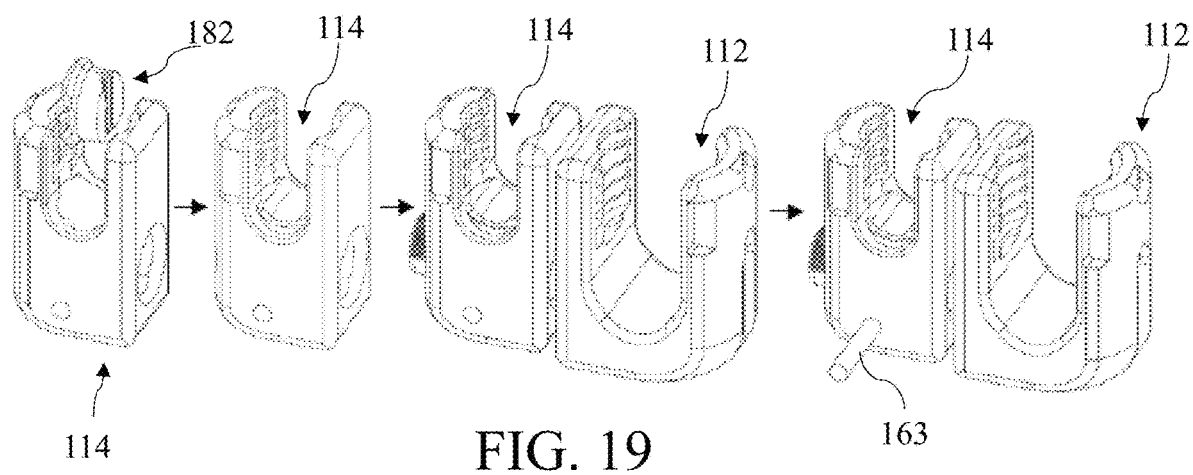
FIG. 19 are perspective views of the first and second clamping portions of the articulating connector shown in FIG. 15 during assembly.

Turning now to FIG. 19, during assembly, the saddle 182 is received in the opening 178 in tulip 114 in a first sideways position and is subsequently turned 90 degrees and pushed further into tulip 114 to a second position. The rod acceptor 112 is then engaged to the tulip 114 by having the projection 140 received within the first opening 176. With the saddle 182 already having been turned 90 degrees and seated, the lower surface 189 will align with the outer surface of the projection 140. In addition, pin 163 is received within the opening 161 after projection 140 is received in the first opening 176. The pin is configured to pass through the cutout 146 of the projection 140. The pin 163, in an exemplary embodiment, is fixed in the opening 161 via an interference fit, via plastic deformation, or by welding or similar permanent fixation. With the pin 163 in place in the opening 161 and the saddle in the second position, the rod acceptor 112 is operatively coupled to the tulip 114 such that the rod acceptor 112 and the tulip 114 can translate and rotate with respect to each other but cannot decouple from each other.

More specifically, and with reference to FIGS. 17A-B, the pin 163 will limit the amount of translation of the rod acceptor 112 with respect to the tulip 114 since the pin 163 will either abut the proximal end or edge 147 or the medial end or edge 149 of the cutout 146 as the rod acceptor 112 translates toward or away from the tulip 114.

Figures 18A, 18B, 18C:
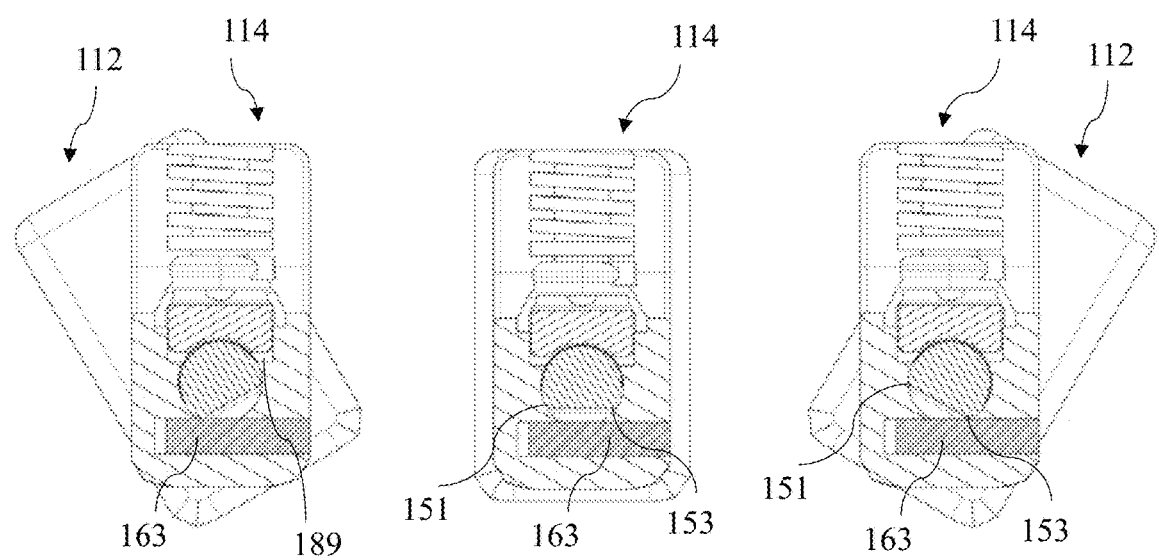
FIGS. 18A-18C are partial cross sectional side views of the articulating connector shown in FIG. 15.

Regarding the limited rotation, with reference to FIGS. 18A-C, with the projection 140 positioned inside the first opening 176, the rod acceptor 112 can rotate relative to the tulip 114. The rotation of the rod acceptor 112 relative to the tulip 114 is limited by the pin 163 and the lateral edges or end 151, 153 of the cutout 146 of the projection 140. As the rod acceptor 112 is rotated, the pin 163 will abut the lateral edges or end 151, 153 of the cutout 146 limiting the rotational travel of the rod acceptor 112 with respect to the tulip 114. In an exemplary embodiment, the rotational travel is limited to 30 degrees in each direction.

In an exemplary use, the tulip 114 and the rod acceptor 112 are adjusted, both translationally and rotationally, so that the rods 150 and 160 can be received within the passageways 120 and 156, respectively. Once the rod 160 is received within passageway 156 between legs 152, 154, the securing mechanism 174 is engaged with the engagement structures 172. This provisionally couples the rod 160 to the tulip 114. Similarly, once the rod 150 is received within passageway 120 between legs 116, 118, the securing mechanism 138 is engaged with the engagement structures 136. This provisionally couples the rod 150 to the rod acceptor 112. Once the tulip 114 is positioned at the desired location on rod 160, the securing mechanism 174 is then further tightened locking the tulip 114 onto the rod 160. As the securing mechanism 174 is further tightened, the securing mechanism 174 pushes on the rod 160, which, in turn, pushes on the saddle 182. As best seen in FIGS. 20A-20B, saddle 182 translates downwardly pushing against the projection 140 locking the rod acceptor 112 both translationally and rotationally with respect to the tulip 114. The texturing 148 and 191 further assist in the locking of the two clamping components. In an exemplary embodiment, a tightening instrument may be used to engage opening 175 to further tighten the securing mechanism 174. Similarly, once the rod acceptor 112 is positioned at the desired location on rod 150, the securing mechanism 138 is then further tightened locking the rod acceptor 112 onto the rod 150. In an exemplary embodiment, a tightening instrument may be used to engage opening 139 to further tighten the securing mechanism 138. It should be noted that there is no order in the process of locking the rods 150 and 160 to the rod acceptor 112 and the tulip 114 and locking the rod acceptor 112 to the tulip 114.

It is contemplated that an open rod connector similar to the open rod connector 94 or a closed rod connector similar to the closed rod connector 95 can be used in place of the rod acceptor 112 in the articulating connector 100.

Figure 21:
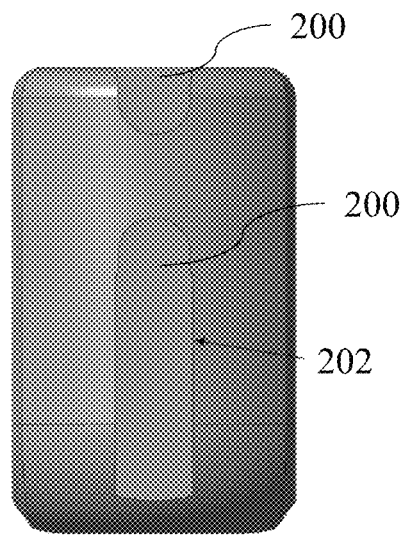
FIG. 21 is a side view of a clamping component according to a fifth exemplary embodiment.
Figure 22:
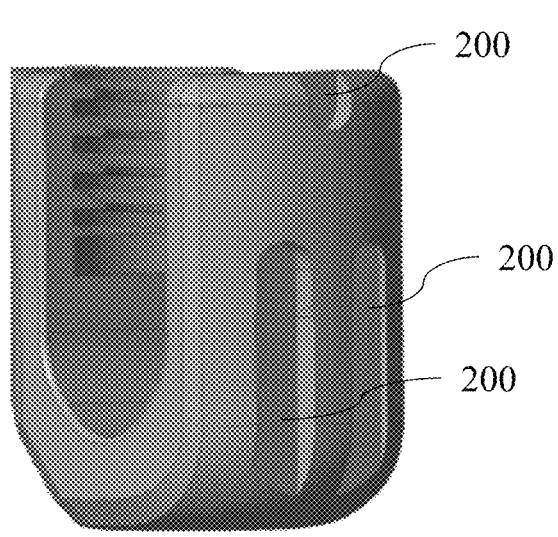
FIG. 22 is a perspective view of a clamping component according to a sixth exemplary embodiment.
Figure 23:
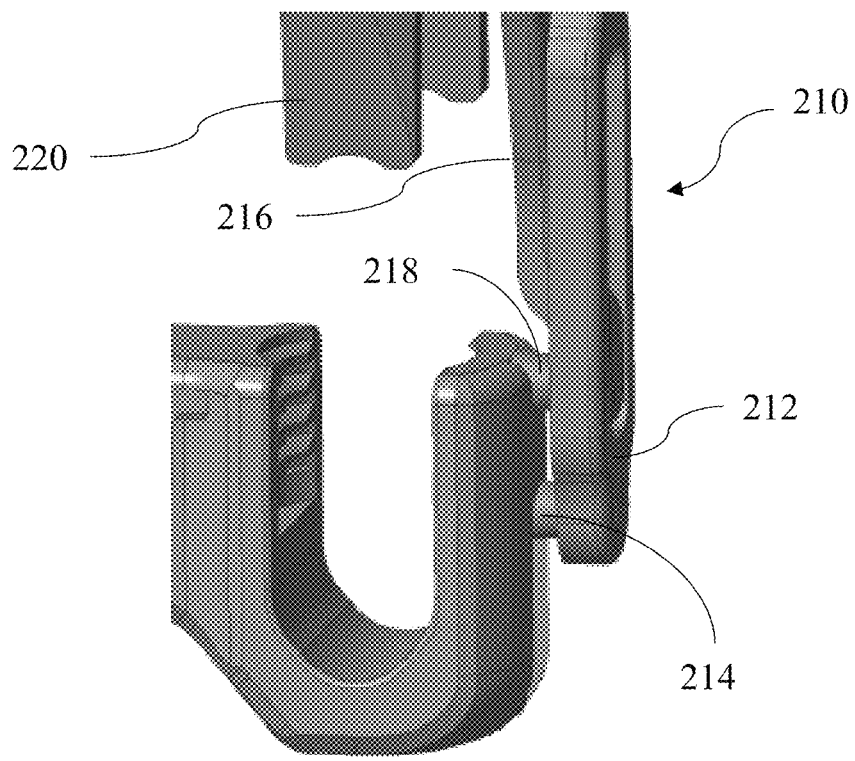
FIG. 23 is a perspective view of an insertion instrument engaged with the clamping component shown in either FIG. 20 or FIG. 21.

With reference to FIGS. 21, 22 and 23, first and/or second clamping portions, such as tulips 14 and 114 and rod acceptors 12 and 112, in an exemplary embodiment, can also include dovetail grooves 200 located on one or more of the outer surfaces 28, 128, 64, and 164 of the tulips 14 and 114 and rod acceptors 12 and 112. The dovetails grooves 200 can also include a clearance cut 202 that cuts away a portion of the dovetail groove 200 for easier engagement or disengagement of a reduction instrument 210. FIG. 20 shows an exemplary embodiment of one dovetail groove 200 located near an upper end of a clamping portion and one dovetail groove located near a bottom end of a clamping portion while FIG. 21 shows an exemplary embodiment of one dovetail groove 200 located near an upper end of a clamping portion and two dovetail grooves located near a bottom end of a clamping portion.

The embodiment shown in FIG. 21 uses a pair of coaxial and coplanar dovetails 200. When the reduction instrument 210 is connected to the clamping portion through the dovetails 200 and pins 214 and 218, the primary pinching action when the reduction instrument 210 attaches to the clamping portion, grips the clamping portion, and the dovetails 200 further support lateral and torsional loads. More specifically, the reduction instrument 210 has two pins 214 and 218, which are conical in an exemplary embodiment, that engage the dovetails 200 of the clamping portion. In terms of engagement, a first engagement element 216 engages the clamping portion dovetail 200 via pin 218. A second engagement element 212 then slides pin 214 upwardly into place in dovetail 200. Once fully engaged, the reducer 220 can then move and push against a rod, such as rods 50, 150, 60, 160 to fully seat the rod in the clamping portion. To disengage the reduction instrument 210, the second engagement element 212 slides downwardly disengaging pin 214 from the dovetail 200. Although not discussed with respect to the embodiment shown in FIG. 22, the engagement, disengagement and reduction of a rod is that same as described with respect to the embodiment shown in FIG. 21.

The articulating connectors described herein offer versatility in connecting spinal rod implants together. In the case of an existing construct being accessed in a revision surgery, the new fixation constructs may be attached without the need to remove the original surgical hardware. Attaching directly to existing spinal rod constructs saves operating time, causes less disruption to the patient, and improves patient healing times. The connectors maximize utility in cases of varying patient anatomy and different configurations for existing constructs. The different connection modes offer a wide range of options for improved patient outcomes.

It will be further understood that various changes in the details, materials, and arrangements of the parts which have been described and illustrated in order to explain the nature of this invention may be made by those skilled in the art without departing from the scope of the invention as expressed in the claims.

What is claimed is:

1. A connector system comprising:
   a connector having a body having a first clamping portion and a second clamping portion;

the first clamping portion having:
a first passageway having a first longitudinal axis extending therethrough and being sized to allow a first rod to be inserted therein;
a bottom portion having a first opening in communication with the first passageway;
two opposing legs, the first passageway defined between the two opposing legs; and
a first securing mechanism positioned at least in part in the first passageway, the first securing mechanism capable of moving from a first position to a second position; and
the second clamping portion having:
a second passageway having a second longitudinal axis extending therethrough and being sized to allow a second rod to be inserted therein;
a post extending from the second clamping portion and having a partially cylindrical outer surface, the post being configured and
dimensioned to be received in the first opening,
wherein the first clamping portion and second clamping portion are configured to rotate and/or translate relative to each other,
wherein the first clamping portion includes a second opening configured to receive a pin, the pin is positioned perpendicularly to the post and positioned under the post, wherein the pin is positioned perpendicular to a longitudinal axis of the first clamping portion, and wherein the pin is configured to engage with the post to limit translation and rotation of the post.

2. The system of claim 1, wherein the second clamping portion comprises two opposing legs, the second passageway defined between the two opposing legs.

3. The system of claim 1, further comprising a locking cap configured and dimensioned to engage the opposing legs of the first clamping portion after the first rod is received in the first passageway.

4. The system of claim 3, wherein rotation of the locking cap results in the locking cap pushing on the first rod which results in the first rod pushing on the securing mechanism moving the securing mechanism from the first position to the second position, wherein in the second position, the securing mechanism prevents movement of the first clamping portion with respect to the second clamping portion.

5. The system of claim 4, wherein the securing mechanism is a saddle comprising a projection portion.

6. The system of claim 1, wherein the second rod is larger than the first rod.

7. The system of claim 1, wherein the first clamping portion and the second clamping portion each have outer surfaces and wherein at least one of the outer surfaces of the first clamping portion and the second clamping portion includes a pair of dovetails for engaging with a reduction instrument.

8. A connector system comprising:
a connector having a body having a first clamping portion and a second clamping portion;
the first clamping portion having:
a first passageway having a first longitudinal axis extending therethrough and being sized to allow a first rod to be inserted therein;
a bottom portion having a first opening in communication with the first passageway and a second opening configured and dimensioned to receive a pin member;
two opposing legs, the first passageway defined between the two opposing legs; and
a first securing mechanism positioned at least in part in the first passageway, the first securing mechanism capable of moving from a first position to a second position; and
the second clamping portion having:
a second passageway having a second longitudinal axis extending therethrough and being sized to allow a second rod to be inserted therein;
a post extending from the second clamping portion, the post being configured and dimensioned to be received in the first opening,
wherein the first clamping portion and second clamping portion are configured to rotate and/or translate relative to each other
wherein the pin member is positioned perpendicularly to the post and positioned, wherein the pin member is positioned perpendicular to a longitudinal axis of the first clamping portion, and wherein the pin member is configured to engage with the post to limit translation and rotation of the post.

9. The system of claim 8, wherein the post has a cutout on a lower surface, the cutout configured and dimensioned to engage with the pin member to limit translation and rotation of the first clamping portion relative to the second clamping portion.

10. The system according to claim 8, wherein the post has an upper surface that includes texturing.

11. The system of claim 8, further comprising a locking cap configured and dimensioned to engage the opposing legs of the first clamping portion after the first rod is received in the first passageway.

12. The system of claim 11, wherein rotation of the locking cap results in the locking cap pushing on the first rod which results in the first rod pushing on the securing mechanism moving the securing mechanism from the first position to the second position, wherein in the second position, the securing mechanism prevents movement of the first clamping portion with respect to the second clamping portion.

13. The system of claim 8, wherein the second clamping portion comprises two opposing legs, the second passageway defined between the two opposing legs.

14. The system of claim 13, further comprising a locking cap configured and dimensioned to engage the opposing legs of the second clamping portion after the second rod is received in the second passageway.

* * * * *